United States Patent [19]

Pierce et al.

[11] Patent Number: 4,758,158
[45] Date of Patent: Jul. 19, 1988

[54] HYDROCOLLOID INJECTION SYSTEM

[75] Inventors: James E. Pierce, Newbury Park; Daniel N. Kottler, Camarillo, both of Calif.

[73] Assignee: Sol Belport Company, Inc., Camarillo, Calif.

[21] Appl. No.: 544,231

[22] Filed: Oct. 21, 1983

[51] Int. Cl.$^4$ ............................................. A61C 5/04
[52] U.S. Cl. ................................................... 433/90
[58] Field of Search ................................. 433/90, 225

[56] References Cited

U.S. PATENT DOCUMENTS

| | | | |
|---|---|---|---|
| 2,265,118 | 12/1941 | Van Rossem | 18/47 |
| 2,505,028 | 4/1950 | Boeger | 433/90 |
| 2,903,794 | 9/1959 | Carfagni | 433/90 |
| 2,991,224 | 7/1961 | Bell | 167/60 |
| 3,191,809 | 6/1965 | Schultz et al. | 222/567 |
| 3,345,497 | 10/1967 | Porteous | 219/417 |
| 3,346,147 | 10/1967 | Higgins | 433/90 |
| 3,731,453 | 5/1973 | Porteous | 53/37 |
| 3,760,503 | 9/1973 | Baskas | 433/90 |
| 4,232,688 | 11/1980 | Day | 132/91 |
| 4,260,597 | 4/1981 | Porteous | 424/49 |

Primary Examiner—Robert Peshock
Attorney, Agent, or Firm—Jack C. Munro

[57] ABSTRACT

The hydrocolloid injection system which utilizes a dispensing syringe as the vial within which the hydrocolloid impression material is shipped and stored prior to usage. The syringe includes a transparent barrel within which the hydrocolloid material is located. A plunger is slidingly mounted within the barrel which is to function to cause the hydrocolloid material to flow from the barrel through an outlet opening. The plunger forms an airtight and watertight seal with respect to the barrel with also a cap being located about the outlet opening of the barrel also forming an airtight and watertight seal. The barrel, plunger and cap can all be located within boiling water with no fear of the water itself actually coming into contact with the hydrocolloid impression material. During usage, the cap will be removed and a nozzle assembly mounted in conjunction with the barrel to facilitate depositing of the hydrocolloid impression material at its desired location.

1 Claim, 1 Drawing Sheet

U.S. Patent  Jul. 19, 1988  4,758,158
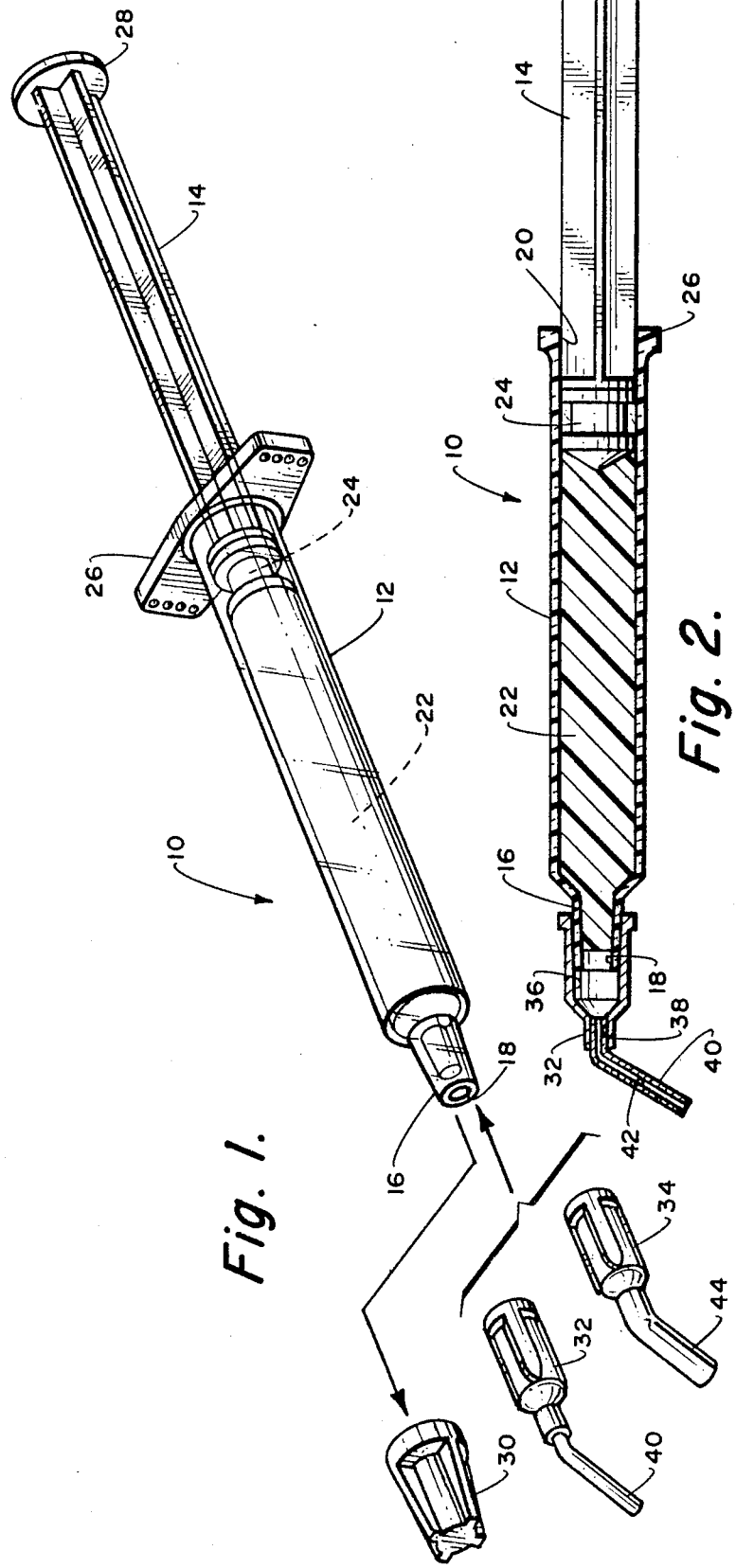
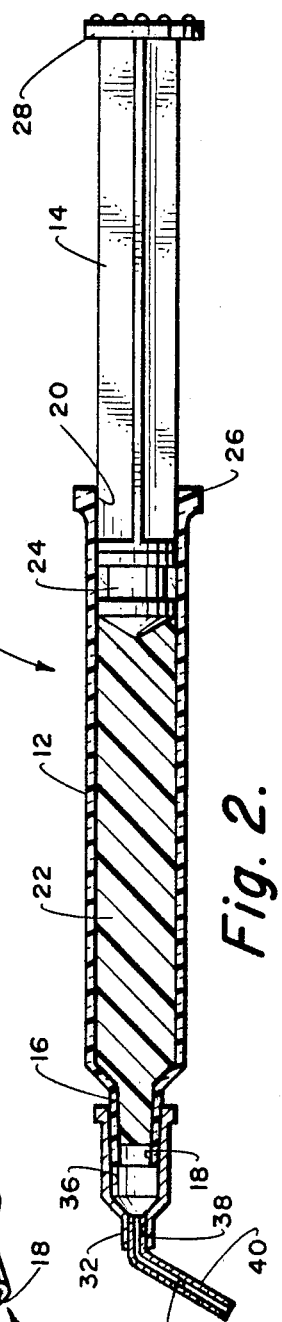
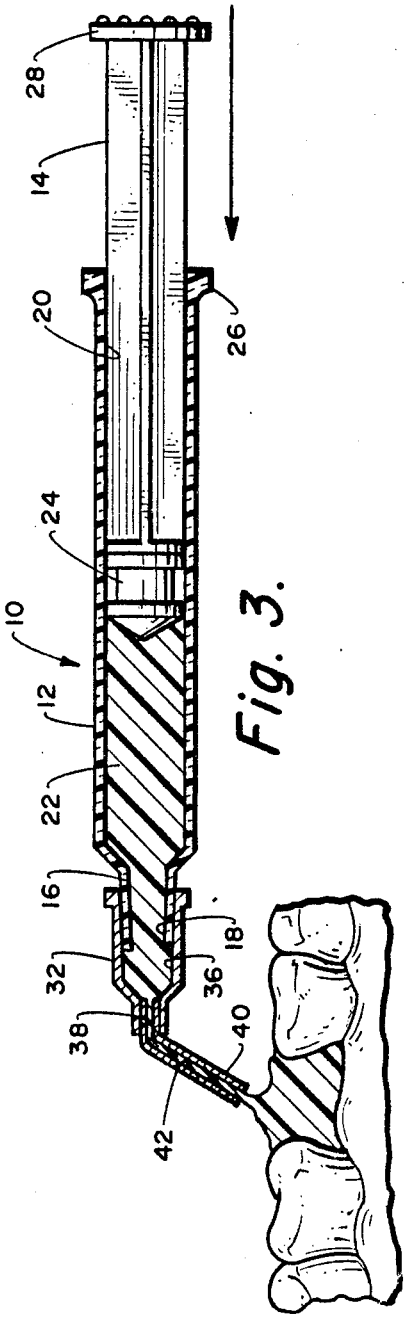

HYDROCOLLOID INJECTION SYSTEM

BACKGROUND OF THE INVENTION

The field of this invention relates to hydrocolloid injection systems for manufacturing and using of a reversible hydrocolloid dental impression material.

The use of a reversible hydrocolloid impression material is quite common within the dental field. Such material is used for taking dental impressions for the subsequent construction of inlay, fixed bridge and partial denture. The reversible hydrocolloid impression material is dispensed in liquid form onto the specific dental area at which it is to be desired to make the impression. Within a short period of time the material hardens into a solid. The impression material is then removed and the resulting formed mold is then utilized in the construction of the inlays, bridges or dentures.

The reversible hydrocolloid impression material which is used in dental work is usually comprised of a formulated aqueous suspension of a gum (such as agar agar). This material is a gel (solid) at ordinary temperatures such as 75° to 100° F. If the material is heated to approximately 200° to 212° F., the material becomes liquid and readily flowable. Therefore, the user of the material can inject the material in liquid form to the desired location. Upon the liquid cooling, it will assume the configuration of its environment. Therefore, such material is of significant advantage with taking of a dental impression.

It is necessary to use a tool to cause the liquid impression material to be deposited at confined quartered locations. A desirable type of such a tool has been found to be a syringe. The hydrocolloid material is preformed into the shape of a stick. The stick hydrocolloid material is inserted within the syringe prior to usage. The entire syringe is then immersed in boiling water for a few minutes, until the material becomes liquid form. The syringe is then removed from the boiling water, cooled to a comfortable usable temperature (approximately 150° F.), and is then used by the user to dispense the hydrocolloid material at the desired location. All known prior art systems utilize some form of syringe mechanism, which is then loaded with some form of hydrocolloid material in stick form. The syringe is reusable.

There is also known to use a hydrocolloid filled cartridge in conjuction with an applying tool. Such a cartridge is shown in U.S. Pat. No. 3,731,453, issued to Don D. Porteous. The disadvantages of the cartridge system are: (1) By using a separate dispensing tool with the warmed cartridge, working time is severely limited due to cooling of the cartridge before it can be dispensed; (2) It requires the user to physically load the cartridge into the tool.

The disadvantages of such prior art hydrocolloid injection systems are that the syringe must be cleaned between times of usage. This cleaning is normally time consuming, and if the syringe is not cleaned properly, the syringe may be difficult to use at the next usage. Also, periodic maintenance of reusable parts of the syringe is required. Further, this prior hydrocolloid injection system required a supply of hydrocolloid injection sticks and these sticks must be contained within an airtight container to prevent the sticks from drying out. Still further, in loading the syringe, air may be entrapped, which during boiling can expand and discharge the syringe plunger ruining the hydrocolloid material. Additionally, entrapped air during dispensing will ruin the impression.

It would be desirable to utilize a hydrocolloid injection system wherein the hydrocolloid material is preloaded within each individual dispensing mechanism and, upon the hydrocolloid material having been dispensed, the dispensing mechanism can be merely discarded. Utilizing of the dispensing mechanism as also the storage container eliminates the need and expense of such storage containers, as well as eliminates the need to load the dispensing mechanism. Also, it would be desirable to design the dispensing mechanism to be inexpensive to manufacture and therefore, inexpensive to use, even though the dispensing mechanism is just discarded after a single use.

SUMMARY OF THE INVENTION

One object of the present invention is to construct a hydrocolloid injection system wherein the dispensing mechanism is preloaded with the hydrocolllloid injection material, thereby eliminating the need for any assembly steps prior to utilizing of the hydrocolloid material.

Another advantage of the hydrocolloid injection sytem of the present invention is that there is not required any cleaning even if this system is reused.

The hydrocolloid injection system of the present invention also achieves the aforementioned desirable objectives which are mentioned in the last paragraph of the background of the invention.

The structure of the present invention takes the form of a disposable type of transparent syringe which is formed of a barrel within which is slidingly located a plunger. The barrel is to be previously loaded with a quantity of hydrocolloid impression material. The barrel includes an outside opening which is formed within a sleeve. The plunger forms a watertight and airtight seal with the barrel. A cap is mounted about the sleeve also forming a watertight and airtight connection. The cap is used to close the outlet opening prior to usage in order to keep the hydrocolloid impression material in a moist state. A noizzle assembly is to be connected with the sleeve in a tight connection after removal of the cap. The nozzle assembly is to function to direct the hydrocolloid material to a particular location. The entire syringe is to be merely thrown within boiling water for a few minutes prior to usage in order to heat the hydrocolloid material so that it will flow in liquid form through the outlet opening.

BRIEF DESCRIPTION OF THE DRAWING

FIG. 1 is an isometric view, partially exploded, of the hydrocolloid injection system of the present invention showing a removable cap which is to normally close the dispensing opening of the syringe and depicting of various sizes of nozzle assemblies which the user might have available to choose from to connect with the syringe;

FIG. 2 is a longitudinal, cross-sectional view through the syringe of the present invention showing the plunger in position prior to dispensing of any of the hydrocolloid impression material within the barrel of the syringe; and FIG. 3 is a cross sectional view similar to FIG. 2 but showing depositing of the hydrocolloid impression material at a particular dental location.

DETAILED DESCRIPTION OF THE SHOWN EMBODIMENT

Referring particularly to the drawing, there is shown a syringe 10 which is constructed generally of a barrel 12 and a plunger 14. The barrel 12 is constructed of transparent plastic and is cylindrical in transverse cross sectional configuration. The fore end of the barrel 12 is integrally connected to a smaller diametered sleeve 16. Within the sleve 16 is an outlet opening 18. The exterior surface of the sleeve 16 is slightly tapered forming a smaller diametered section at its free outer end.

Within the aft end of the barrel 12 there is formed an enlarged opening 20. A quantity of hydrocolloid impression material 22 is to be inserted through the outlet opening 18 and to be confined within the barrel 12. The hydrocolloid impression material 22 forms no specific part of this invention and is deemed to be conventional.

Also located through the enlarged opening 20 and positioned within the barrel 12 is the inner end of the plunger 14. The inner end of the plunger 14 is formed into a resilient tip 24. The resilient tip 24 forms an airtight and watertight seal with the barrel 12. The plunger 14 is to be movable within the barrel 12 while maintaining this airtight and watertight seal. The desirable material of construction for the tip 24 would be rubber. During loading of barrel 12 with the heated hydrocolloid material, the plunger 14 is moved from a position directly adjacent sleeve 16 to a rear position shown in FIG. 1.

Attached to the back end of the barrel 12 is an enlarged flange 26. Two of the operators fingers are to be located against the flange 26, with the thumb of the operator being placed against the back flange 28 of the plunger 14. Manual force being exerted against the back flange 28 would then cause the plunger 14 to move wthin the barrel 12. If the impression material 22 is flowable, that material then would be forced through the outlet opening 18. It is to be understood that for the impression material 22 to be flowable, it is necessary that the entire syringe 10 be submerged within boiling water for a period of a few minutes.

During storage prior to usage of the syringe 10, it is necessary that hydrocolloid impression material be protected from drying out and also when placed within the boiling water, that the water does not come into direct contact with the impression material 22. The tip 24 of the plunger 14 functions to provide the necessary seal in respect to the enlarged opening 20. In order to achieve the same type of seal about the outlet opening 18, there is utilized a cap 30. The cap 30 is to tightly connect with the tapered exterior surface of sleeve 16 forming an airtight and watertight connection therebetween.

The cap 30 can be readily removed at the time syringe 10 is to be used. The operator then connects a nozzle assembly, such as nozzle assembly 32 or 34, with the sleeve 16. The tapered exterior surface of the sleeve 16 forms a snug fit with the interior wall 36 of the nozzle assembly 32. The interior wall 36 forms an interior chamber which connects with oriface 38. Tightly interfitting within the orifice 38 is a tube 40. Tube 40 includes an inner passage 42. Hydrocolloid impression material is to be forced through the passage 42 and is directed to confined dental areas by the tube 42 such as shown within FIG. 3 of the drawing.

Nozzle assembly 34 also includes a tube 44 similar to tube 40. The distinction betwen the nozzle assemblies 32 and 34 is that tube 44 has a slightly greater diameter of passage, such as passage 42 for tube 40. The operator can freely select the desired size of passage to be utilized for the particular usage requirement.

It is to be understood that after the hydrocolloid impression material 22 has been substantially dispensed from within the barrel 12 or that the usage of the particular syringe 10 for the particular situation is no longer needed, the operator need only to discard the entire syringe 10. Upon hydrocolloid impression material again being needed, it is only necessary for the user to utilize an unused syringe.

It is to be understood that the nozzle assemblies 32 and 34 may be reused. It is also to be understood that if the impression material is not substantially disposed, the nozzle assembly is removed and the sleeve 16 can be reflected by cap 30 permitting reusage of the syringe.

What is claimed is:

1. A hydrocolloid injection system comprising:
   a quantity of hydrocolloid impression material;
   a syringe, having a barrel in which is slidingly located a plunger, said barrel terminating at an outlet opening, said hydrocolloid impression material being located within said barrel, said syringe being constructed of transparent plastic so as to be readily able to visually observe the quantity of hydrocolloid material within said barrel;
   a sleeve attached to said barrel around said outlet opening, said hydrocolloid impression material being conductable through said sleeve, said sleeve having an exterior surface;
   a cap removably connected to said exterior surface, said cap to form a first watertight and airtight seal with said sleeve, said plunger forming a second watertight and airtight seal with said barrel, whereby said syringe is to be locatable within boiling water to cause the hydrocolloid material to be flowable through said outlet opening and the boiling water does not intermix with said hydrocolloid material; and
   a nozzle assembly, said hydrocolloid material to be dispensed through said nozzle assembly into the ambient, said nozzle assembly being attached to said sleeve upon said cap having been removed from said sleeve, there being a plurality of different sizes of nozzle assemblies with any one of said nozzle assemblies to be selected to be connected to said sleeve.

* * * * *